US009695100B1

(12) United States Patent
Kockrick et al.

(10) Patent No.: US 9,695,100 B1
(45) Date of Patent: Jul. 4, 2017

(54) METHOD FOR THE PRODUCTION OF MIXTURES CONTAINING TERTIARY ISONONANOIC ACIDS BASED ON 2-ETHYLHEXANOL

(71) Applicant: Oxea GmbH, Oberhausen (DE)

(72) Inventors: Kristina Kockrick, Düssseldorf (DE); Leif Johnen, Dorsten (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 15/311,676

(22) PCT Filed: Jun. 26, 2015

(86) PCT No.: PCT/EP2015/001290
§ 371 (c)(1),
(2) Date: Nov. 16, 2016

(87) PCT Pub. No.: WO2016/029978
PCT Pub. Date: Mar. 3, 2016

(30) Foreign Application Priority Data

Aug. 30, 2014 (DE) ........................ 10 2014 013 123

(51) Int. Cl.
*C07C 51/00* (2006.01)
*C07C 53/128* (2006.01)
*C07C 51/373* (2006.01)

(52) U.S. Cl.
CPC .......... *C07C 51/373* (2013.01); *C07C 53/128* (2013.01)

(58) Field of Classification Search
CPC .............................. C07C 5/001; C07C 53/128
See application file for complete search history.

(56) References Cited

U.S. PATENT DOCUMENTS

| 6,281,372 B1 | 8/2001 | Wiese |
| 6,433,217 B1 | 8/2002 | Rosenbrand |
| 6,433,242 B1 | 8/2002 | Wiese |
| 9,174,922 B2 | 11/2015 | Johnen |

FOREIGN PATENT DOCUMENTS

| DE | 1142167 | * | 1/1963 |
| DE | 1142167 B | | 1/1963 |
| DE | 2406223 A1 | | 8/1975 |
| DE | 19906518 A1 | | 8/2000 |
| DE | 19908320 A1 | | 8/2000 |
| DE | 102012002282 A1 | | 8/2013 |
| DE | 102013009323 A1 | | 12/2014 |
| EP | 0497340 A2 | | 8/1992 |
| WO | 2014191090 A1 | | 12/2014 |

OTHER PUBLICATIONS

Reutemann et al, Formic Acid, Ullmann's Encyclopedia of Industrial Chemistry, Published Online: Oct. 15, 2011, pp. 13-33.*
Ullmanns Encyklopädie der technischen Chemie, 4th Edition, 1975, pp. 145-146, vol. 9, Verlag Chemie, Weinheim/Bergstr., Germany.
Ullmanns Encyklopädie der technischen Chemie, 4th Edition, 1976, pp. 89-97, vol. 11, Verlag Chemie, Weinheim/Bergstr., Germany.
Ullmanns Encyklopädie der technischen Chemie, 4th edition, 1983, pp. 421-424, vol. 23, Verlag Chemie, Weinheim/Bertgstr., Germany.
Ullmanns Encyklopädie der technischen Chemie, 4th Edition, 1983, pp. 606-607, vol. 23, Verlag Chemie, Weinheim/Bertgstr., Germany.
Ullmann's Encyclopedia of Industrial Chemistry, 6th Ed., 2003, pp. 502-503, vol. 6, Wiley-VCH Verlag GmbH & Co. KGaA, Weinheim, Germany.
Ullmann's Encyclopedia of Industrial Chemistry, 6th Ed., 2003, p. 643, vol. 24, Wiley-VCH-Verlag GmbH, Germany.
Encyclopedia of Industrial Chemistry, 4th Edition, 1974, pp. 214-215, vol. 7, Verlag Chemie.
Ullmann's Encyclopedia of Industrial Chemistry, 6th Ed., 2003, pp. 70-73, vol. 38, Wiley-VCH Verlag GmbH & Co. KGaA, Weinheim, Germany.
Kirk-Othmer Encyclopedia of Chemical Technology, 3rd edition, 1983, p. 190, vol. 22, John Wiley & Sons, New York.
K. Weissermel, H. Arpe, Industrielle Organische Chemie, 3rd Edition, 1988, pp. 74-79, VCH Verlagsgesellschaft mbH, Weinheim, Germany.
K. Weissermel, H. Arpe, Industrielle Organische Chemie [Industrial Organic Chemistry], 3rd edition, 1988, p. 152, VCH Verlagsgesellschaft mbH, Weinheim, Germany.
Houben-Weyl—Methoden der Organischen Chemie, 4th edition, 1952, pp. 547-549, vol. VIII, Georg Thieme Verlag, Stuttgart.
Houben-Weyl—Methoden der Organischen Chemie [Methods of Organic Chemistry], 4th Edition, 1958, pp. 10-14, 16-19, vol. XI/2, Georg Thieme Verlag, Stuttgart.
Falbe, "Carbonylation with Acid Catalysts Koch Reaction", Carbon Monoxide in Organic Synthesis, 1970, pp. 137-143, vol. 10, Springer-Verlag Berlin, Heidelberg, New York.
H. Koch, et al., "Synthese der cis-Decalincarbonsäure-9", Angewandte Chemie, May 21, 1958, p. 311, vol. 70, Issue 10, Wiley-VCH Verlag GmbH & Co. KGaA, Weinheim, Germany.
G. Scharfe, "Convert butenes to high octane oligomers", Hydrocarbon Processing, Apr. 1973, pp. 171-173.
Römpps Chemie-Lexikon, 8th edition, 1987, pp. 3651-3654, vol. 5, Frank'sche Verlagshandlung, Stuttgart.
G. Hubner, "Vinylierung höherer Carbonsäuren an Katalysatorschmelzen", Fette, Seifen, Anstrichmillel, 1966, pp. 290-292, vol. 68, Issue 4.
H. Koch et al., "Über die Synthese verzweigter Carbonsäuren nach der Ameisensäure-Methode", Justus Liebigs Annalen der Chemie, Nov. 1958, pp. 250-267, vol. 618, Issue 1.

(Continued)

*Primary Examiner* — Paul A Zucker

(74) *Attorney, Agent, or Firm* — Michael W. Ferrell

(57) ABSTRACT

A process for producing a mixture comprising tertiary isononanoic acids proceeding from 2-ethylhexanol is characterized in that 2-ethylhexanol is (a) reacted at a temperature of 0° C. to 40° C. with a mixture of concentrated formic acid and a concentrated Brønsted acid, wherein 2 to 10 mol of formic acid are used per mole of 2-ethylhexanol and the concentrated Brønsted acid is used in an amount that corresponds to 6 to 90 mol of protons per mole of 2-ethylhexanol. The resulting reaction mixture from step (a) is subsequently (b) brought into contact with water, and the mixture comprising tertiary isononanoic acids formed according to step b) is removed.

20 Claims, No Drawings

(56) References Cited

OTHER PUBLICATIONS

Ullmann's Encyclopedia of Industrial Chemistry, 5th Ed., 1989, pp. 26-27, vol. A12, VCH Verlagsgesellschaft mgH, Weinheim, Germany.

* cited by examiner

METHOD FOR THE PRODUCTION OF MIXTURES CONTAINING TERTIARY ISONONANOIC ACIDS BASED ON 2-ETHYLHEXANOL

CLAIM FOR PRIORITY

This application is a national phase application of PCT/EP2015/001290 FILED Jun. 26, 2015 which was based on application DE 10 2014 013 123.8 FILED Aug. 30, 2014. The priorities of PCT/EP2015/001290 and DE 10 2014 013 123.8 are hereby claimed and their disclosures incorporated herein by reference.

TECHNICAL FIELD

The present invention relates to the production of mixtures comprising tertiary isononanoic acids proceeding from 2-ethylhexanol by reacting 2-ethylhexanol with a mixture of concentrated formic acid and a concentrated Brønsted acid.

BACKGROUND

Tertiary isononanoic acids are understood to mean positional isomers of aliphatic carboxylic acids having nine carbon atoms in the molecule, in which the α-carbon atom adjacent to the carboxyl group bears two alkyl groups in addition to the main chain. This α-carbon atom bears a total of four substituents and is often also referred to as a quaternary carbon atom. An industrially important representative of such a positional isomer of isononanoic acid is 2,2,4,4-tetramethylpentanoic acid. Preparation of the latter is carried out by hydroxycarbonylation or the so-called Koch reaction of industrially available diisobutene with sulfuric acid at elevated carbon monoxide pressure. (Ullmann's Encyclopedia of Industrial Chemistry, 6th Ed., Vol. 6, pp. 502-503, 2003 Wiley-VCH Verlag GmbH & Co. KGaA, Weinheim).

Also of industrial importance are the so-called Versatic acids 9 from Momentive Specialty Chemicals Inc., the structure of which may be described as follows:

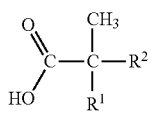

where $R^1$ and $R^2$ are alkyl groups comprising 6 carbon atoms in total.

In addition to the use of the dimers of isobutene, the dimers of n-butene are also described as starting material for the preparation of tertiary isononanoic acids. According to DE 199 06 518 A1, octenes from the dimerization of n-butenes are also converted with carbon monoxide and water to the tertiary isononanoic acids by means of the Koch reaction catalyzed by strong acids. The composition of the isononanoic acid mixture depends on the isomeric composition of the di-n-butene. In addition to an isononanoic acid mixture obtained from the Koch reaction of an unfractionated di-n-butene, DE 199 06 518 A1 also describes the composition of isononanoic acids based on di-n-butenes which are obtained as a more highly branched top fraction and as a less branched bottom fraction during the fractionation of di-n-butene. The reported isononanoic acid mixtures comprise 2-ethyl-2-methylhexanoic acid as the main component in varying amounts. The published German patent application DE 10 2013 009 323 A1 likewise relates to the production of a mixture comprising tertiary isononanoic acids proceeding from an octene mixture as starting material. The octene mixture is obtained by the dehydration of 2-ethylhexanol and is subsequently reacted with carbon monoxide at elevated pressure in the presence of acidic catalysts.

The mixtures of tertiary isononanoic acids obtained are useful intermediates in industrial organic chemistry due to their high degree of branching at the α-carbon atom, which are processed to give a multitude of conversion products for a wide variety of different fields of use. For example, the salts thereof are used as drying accelerators or siccatives for coatings.

The esters of the tertiary isononanoic acids have a high resistance to hydrolysis and oxidation, and the polyol esters thereof, their glycol and polyglycol esters for example, are used as hydraulic fluids and lubricants. Tertiary isononanoic acids may also be derivatized to vinyl esters, either by reaction with acetylene in the presence of zinc salts at temperatures of 200 to 230° C. or by the transition metal-catalyzed transvinylation reaction with a vinyl ester of another carboxylic acid, usually vinyl acetate or vinyl propionate (Ullmann's Encyclopedia of Industrial Chemistry, 6th Ed., Vol. 38, pp. 70-73, 2003 Wiley-VCH Verlag GmbH & Co. KGaA, Weinheim). Vinyl esters have a certain commercial significance as the monomer component in homo- and copolymers. As comonomers, they can modify the properties of polymers such as polyvinyl acetate, polyvinyl chloride, polystyrene or polyacrylic esters. The corresponding copolymers can be processed to give paints which feature an improved resistance to hydrolysis and relatively low moisture absorption. Vinyl esters of tertiary isononanoic acids are also used for preparing adhesives. Tertiary isononanoic acids can also be converted to glycidyl esters, for example by reaction with epichlorohydrin in the presence of sodium hydroxide by the method described in U.S. Pat. No. 6,433,217 B1 (Kirk-Othmer, Encyclopedia of Chemical Technology, $3^{rd}$ Ed., Vol. 5, John Wiley & Sons 1979). Industrially, glycidyl esters of tertiary carboxylic acids are used, for example, for modifying alkyd resins or for producing color-stable coating compositions for exterior applications. (Weissermel, Arpe, Industrielle Organische Chemie [Industrial Organic Chemistry], VCH Verlagsgesellschaft, $3^{rd}$ edition, 1988, page 152; Ullmann's Encyclopedia of Industrial Chemistry, $6^{th}$ Ed., Vol 24, Wiley-VCH-Verlag GmbH 2003, page 643).

It is also known that the reaction of olefins to give a mixture of tertiary carboxylic acids in strongly acidic medium is possible, even without applying pressure, when carried out in the presence of concentrated formic acid as carbon monoxide source. This variant, known also as the Koch-Haaf method, may also be extended successfully even to alcohols as starting substances. (Falbe, Carbon Monoxide in Organic Synthesis, Springer Verlag Berlin, Heidelberg, N.Y., 1970, pages 137-143; Angew, Chem., 70, 1958, page 311; Fette, Seifen, Anstrichmittel [Fats, Soaps, Paints] 59, 1957, pages 493-498). According to Liebigs Ann. Chem. 618, 1958, pages 251-266, the reaction of 2-methylbutanol affords, in addition to the expected 2,2-dimethylbutyric acid, other acids such as trimethylacetic acid and C7 acids and also a considerable proportion of higher, mainly C11 acids, which may be derived from a pentene dimer.

The raw material used for the industrial preparation of tertiary isononanoic acids is the C4 cut from the steamcracking of naphtha. The availability thereof compared to the C2 and C3 cracking products can be controlled by the conditions of steamcracking and is guided by the market conditions.

1,3-Butadiene is first removed from the C4 cracking products by extraction or by selective hydrogenation to n-butenes. The resulting C4 raffinate, also called raffinate I, comprises predominantly the unsaturated butenes isobutene, 1-butene and 2-butene, and the hydrogenated products n-butane and isobutane. Isobutene is removed from raffinate I in the next step, for example by reversible proton-catalyzed addition of water to give tertiary butanol, and the resulting isobutene-free C4 mixture is referred to as raffinate II. Isobutene can be recovered again from tertiary butanol by redissociation (Weissermel, Arpe, Industrielle Organische Chemie, VCH Verlagsgesellschaft, 3rd Edition, 1988, pages 74-79). It is likewise possible to contact the butadiene-free C4 raffinate at elevated temperature and under pressure with an acidic suspended ion exchanger. Isobutene oligomerizes to diisobutene, triisobutene, and in a small proportion to higher oligomers. The oligomers are separated from the unreacted C4 compounds. It is then possible to obtain diisobutene or triisobutene in pure form by distillation from the oligomerized material. The dimerization of n-butenes with isobutene forms co-dimer to a small degree (Weissermel, Arpe, Industrielle Organische Chemie, VCH Verlagsgesellschaft, 3rd Edition, 1988, p. 77; Hydrocarbon Processing, April 1973, pages 171-173).

Diisobutene, either prepared by the oligomerization of pure isobutene obtained by redissociation or obtained in the course of workup of a butadiene-free raffinate I, is then converted to a C9 derivative lengthened by one carbon atom. In this case, diisobutene is converted by the abovementioned hydroxycarbonylation or Koch reaction with carbon monoxide and water in the presence of sulfuric acid to the highly branched isononanoic acid 2,2,4,4-tetramethyl-1-pentanoic acid. Owing to the double alkyl branch at the carbon atom adjacent to the carboxyl group, this positional isomer of isononanoic acid is frequently also referred to as neononanoic acid.

The n-butenes present in raffinate II after the isobutene removal are also converted industrially to butene oligomers, from which isomeric octenes are separated, and these are converted via hydroxycarbonylation to the corresponding isononanoic acids (DE 199 08 320 A1; DE 199 06 518 A1). The oligomerization of n-butenes is operated industrially by the DIMERSOL process or by the OCTOL process.

Against the background that the availability of octenes based on the C4 cut from naphtha cracking is limited and depends on the local site conditions, it is desirable to develop further C8 sources based on inexpensively available large-scale products which can be transported to various sites in a simple manner. 2-Ethylhexanol is available inexpensively as an industrial large-scale product which can be sold widely without any problems. As is well known, 2-ethylhexanol is prepared on the industrial scale by hydroformylation or oxo process using propylene to give n-butyraldehyde with subsequent alkali-catalyzed aldol condensation to give 2-ethylhexenal followed by full hydrogenation to give 2-ethylhexanol (Ullmanns Encyklopädie der technischen Chemie [Encyclopedia of Industrial Chemistry], 4th Edition, 1974, Verlag Chemie, Volume 7, pages 214-215). The utilization of 2-ethylhexanol as the C8 source enables the provision of tertiary isononanoic acids based on propylene and reduces dependence on C8 availability based on butene.

The preparation of tertiary isononanoic acids from 2-ethylhexanol is described in DE 1 142 167. According to the known method, a mixture of 2-ethylhexanol and sulfuric acid under carbon monoxide pressure is passed over trickle elements and predominantly 2-ethyl-2-methylhexanoic acid is obtained. The known method operates at high pressures of 500 atm.

SUMMARY OF INVENTION

It has now been found, surprisingly, that 2-ethylhexanol, in the presence of a mixture of a strong Brønsted acid and formic acid under the conditions of the Koch-Haaf reaction, may be converted to a mixture of isomeric isononanoic acids comprising predominantly 2-ethyl-2-methylhexanoic acid, 2,2-dimethylheptanoic acid and small amounts of other positional isomers of tertiary isononanoic acids. High boilers, which can take the form of C17 carboxylic acids from the dimerization of octenes formed as intermediates, followed by hydroxycarbonylation, are surprisingly only formed to a minor degree. This is unexpected since, in the reaction of primary alcohols, the prior art reports extensively on the formation of higher carboxylic acids which can derive from the dimerization of the carbon chain of the alcohol (Liebigs Ann. Chem. 618, 1958, pages 251-266).

The present invention therefore consists in a process for producing a mixture comprising tertiary isononanoic acids proceeding from 2-ethylhexanol, characterized in that
(a) 2-ethylhexanol is reacted at a temperature of 0° C. to 40° C. with a mixture of concentrated formic acid and a concentrated Brønsted acid, wherein 2 to 10 mol of formic acid are used per mole of 2-ethylhexanol and the concentrated Brønsted acid is used in an amount that corresponds to 6 to 90 mol of protons per mole of 2-ethylhexanol,
(b) the reaction mixture obtained according to step a) is subsequently brought into contact with water, and
(c) the mixture comprising tertiary isononanoic acids formed according to step b) is removed.

By way of preference in step a), firstly 2-ethylhexanol and formic acid are mixed and the mixture is added to the initially charged concentrated Brønsted acid. 2 to 10 mol, preferably 3 to 6 mol, of formic acid are used per mole of 2-ethylhexanol. The concentrated Brønsted acid is used in an amount that corresponds to 6 to 90 mol, preferably 12 to 40 mol of protons, per mole of 2-ethylhexanol. Further details are discussed below.

DETAILED DESCRIPTION

The term Brønsted acid is understood to mean the definition customary in the prior art, by which such compounds are referred to as Brønsted acids which are capable of splitting off protons (Römpps Chemie-Lexikon, 8$^{th}$ edition, Frank'sche Verlagshandlung, Stuttgart 1987, volume 5, pages 3651-3654). The strong Brønsted acid used is, for example, sulfuric acid, hydrofluoric acid, phosphoric acid, trifluoromethanesulfonic acid or fluorosulfonic acid and preferably sulfuric acid. The Brønsted acid and the formic acid are used as concentrated acids at a maximum effective concentration, although for practical purposes commercially available concentrated formic acid and sulfuric acid is used. Generally, concentrated formic acid and the concentrated Brønsted acids are commercially available at an effective concentration of 95% by weight and higher (Ullmann's Encyclopedia of Industrial Chemistry, 5$^{th}$ edition, VCH Verlagsgesellscgaft, Weinheim 1989, Vol. A12, page 26;

Kirk-Othmer, Encyclopedia of Chemical Technology, 3$^{rd}$ edition, John Wiley & Sons, New York, 1983, Vol. 22, page 190).

In a preferred configuration of the process according to the invention, commercially available concentrated formic acid, typically at an effective concentration of 95% by weight to 100% by weight, preferably 95% by weight to 98% by weight, and commercially available concentrated sulfuric acid, typically at an effective concentration of 96% by weight to 100% by weight, preferably 96% by weight to 98% by weight, are used, wherein 3 to 6 mol of formic acid are used per mole of 2-ethylhexanol. In this case, sulfuric acid is used in an amount that corresponds to 12 to 40 mol of protons.

The reaction of 2-ethylhexanol with the mixture of formic acid and Brønsted acid in step a) is carried out at temperatures of 0° C. to 40° C., preferably 5° C. to 40° C. and especially 5° C. to 20° C. The reaction components are typically combined over a period of 0.5 to 2 hours; in a preferred configuration, the mixture of 2-ethylhexanol and concentrated formic acid is added over this time period to the initially charged concentrated Brønsted acid. After addition, reaction is allowed to continue over a period of advantageously from 20 to 70 hours, either isothermally at reaction temperature, adiabatically at intrinsic temperature, or initially isothermally at reaction temperature and subsequently adiabatically at intrinsic temperature, for example with continuous stirring or avoiding agitation of the reaction mixture. The mixture of 2-ethylhexanol, formic acid and Brønsted acid is allowed to react at atmospheric pressure or at elevated pressure. Preference is given to operating under atmospheric pressure. If the system is operated at elevated pressure, a positive pressure from above atmospheric pressure to 1 MPa is recommended, preferably a positive pressure of 0.1 to 0.5 MPa. The positive pressure may be established by injecting carbon monoxide or an inert gas, for example, nitrogen. Step a) may also be regarded as carbonylation substep.

On completion of the carbonylation substep, the reaction mixture is subsequently brought into contact with water, for example by adding the reaction mixture to an equivalent volume of water or ice. The step b) in progress here may also be regarded as hydrolysis substep. The bringing into contact with water can take place at the positive pressure at which the carbonylation substep was operated, or the reaction mixture from the carbonylation substep is vented to atmospheric pressure and is brought into contact with water under atmospheric pressure. If the carbonylation substep is already carried out at atmospheric pressure, the hydrolysis substep is also operated advantageously at atmospheric pressure. The organic phase formed in this case, which comprises the mixture containing tertiary isononanoic acids, is separated from the aqueous phase and purified by a water wash.

Without being excessively bound to mechanistic considerations, it may be assumed, in the Koch-Haaf variant, that formic acid is decomposed to carbon monoxide by the dehydrating effect of the concentrated Brønsted acid, in particular of the concentrated sulfuric acid. Furthermore, it can be supposed that 2-ethylhexanol is protonated and a carbenium ion is formed on elimination of water, which further reacts with carbon monoxide, forming an acylium cation. Since the reaction takes place with removal of water, formic acid and Brønsted acid, particularly sulfuric acid, should be used in concentrated form, typically at an effective content of 95 to 98% by weight. Formic acid and Brønsted acids at lower concentrations are not to be recommended due to the excessively high water content.

The reaction mixture obtained according to step a) is subsequently brought into contact with water according to step b), for example, by pouring onto ice. By means of this hydrolysis substep with water or ice, the acylium cation is saturated. In this reaction sequence of carbonylation substep and subsequent hydrolysis substep, which may also be together referred to as hydroxycarbonylation, a mixture of positional isomers of aliphatic isononanoic acids is formed, which bear two α,α-alkyl residues on the carbon atom adjacent to the carboxyl group, and have a so-called neo structure. Such isononanoic acids are also referred to as tertiary isononanoic acids.

The carbonylation substep and the subsequent hydrolysis substep are conducted in conventional reactors for chemical processes, for example, in a stirred tank or in a stirred tank cascade or in a flow tube which may be operated as an empty tube. Alternatively, the flow tube may be provided with static mixers such as beds, packings or internals which enable intensive mixing of the reaction solution. The two steps a) and b) are operated separately, either continuously or batchwise. A biphasic mixture of an aqueous phase and an organic phase is obtained, containing the mixture formed comprising tertiary isononanoic acids. According to step (c), the mixture formed comprising tertiary isononanoic acids is removed, for example by phase separation. The organic product is subsequently washed with water until neutral. By reacting 2-ethylhexanol with formic acid in the presence of concentrated Brønsted acid, present in the resulting mixture of tertiary isononanoic acids, by gas chromatographic analysis according to DIN 51405 (area %), are 2-ethyl-2-methylhexanoic acid as main component and 2,2-dimethylheptanoic acid as secondary component and also low amounts of further positional isomers of aliphatic tertiary isononanoic acids. The proportion of 2-ethyl-2-methylhexanoic acid and 2,2-dimethyl-heptanoic acid is generally more than 90 mol % in total, based on the total content of positional isomers of aliphatic tertiary isononanoic acids.

Surprisingly, tailings components, which are probably higher C17 carboxylic acids, which can arise from the dimerization of the C8 2-ethylhexanol alcohol structure with subsequent reaction with carbon monoxide, are formed only to a minor extent. Their proportion in the crude acid is generally at most 8% (area % by gas chromatography according to DIN 51405).

The purified mixture of positional isomers of aliphatic tertiary isononanoic acids is obtained by means of distillation under conventional conditions from the crude acid mixture removed after the hydroxycarbonylation.

The mixture comprising tertiary isononanoic acids prepared by the process according to the invention can be used, for example, by processes known per se for preparation of derivatives such as the vinyl ester, glycidyl ester, carboxylic esters, isononanoic anhydrides, isononanoyl halides or isononanamides. The vinyl ester is prepared, for example, by reaction of tertiary isononanoic acids with acetylene, preferably in the presence of zinc salts at temperatures of 200-230° C. (G. Hubner, Fette, Seifen, Anstrichmittel 68, 290 (1966), Ullmanns Encyklopädie der technischen Chemie, 4th Edition, 1983, Verlag Chemie, Volume 23, pages 606-607) or by what is called the transvinylation reaction

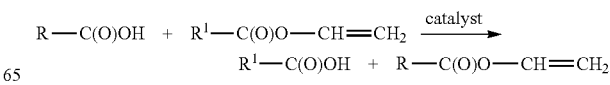

where R is C8 and $R^1$ is frequently methyl or ethyl, and so the transvinylation reagent used is, for example, vinyl acetate or vinyl propionate (Ullmanns Encyklopädie der technischen Chemie, 4th Edition, 1983, Verlag Chemie, Volume 23, pages 606-607). In order to force the chemical equilibrium in the direction of the desired vinyl ester, an excess of the transvinylation reagent $R^1$—C(O)—CH=$CH_2$ is frequently used, and the carboxylic acid formed is simultaneously removed from the reaction mixture. Suitable transvinylation catalysts are compounds of the transition metals from the platinum group ruthenium, osmium, rhodium, iridium, palladium and platinum, especially palladium and ruthenium, which can be used modified with mono- or polydentate organonitrogen or organophosphorus ligands or in unmodified form. Such a process is known, for example, from EP 0 497 340 A2. In the continuous process variant described in DE 10 2012 002 282 A1, the reaction is carried out without removal of a reactant and the reaction mixture discharged is then separated into its constituents.

The resulting vinyl isononanoate based on tertiary isononanoic acids is suitable as a comonomer, for example in polyvinyl acetate, polyvinyl chloride, polystyrene or polyacrylic esters.

The corresponding glycidyl ester can likewise be prepared from the isononanoic acid mixture prepared in accordance with the invention, for example by reaction with epichlorohydrin in the presence of sodium hydroxide, by processes known per se, and this can serve for modification of alkyd resins or for the preparation of color-stable coating compositions (Weissermel, Arpe, Industrielle Organische Chemie, VCH Verlagsgesellschaft, 3rd Edition, 1988, page 152; U.S. Pat. No. 6,433,217; Ullmann's Encyclopedia of Industrial Chemistry, Vol. 24, $6^{th}$ Ed, Wiley-VCH-Verlag GmbH, page 643).

The mixture of tertiary isononanoic acids prepared in accordance with the invention can likewise be reacted with mono- or polyhydric alcohols in a manner known per se to give the corresponding carboxylic esters (Ullmanns Encyklopädie der technischen Chemie, 4th Edition, 1976, Verlag Chemie, Volume 11, pages 89-96), which can be used in lubricant compositions, as a plasticizer for thermoplastic polymers or as a coalescent in emulsion paints. The mixture of tertiary isononanoic acids prepared in accordance with the invention is also suitable for the preparation of oil-soluble metal soaps which are used as dessicants or drying agents (Ullmann's Encyklopädie der technischen Chemie, 4th edition 1983, Verlag Chemie, Vol 23, pages 421-424).

It is likewise possible to derivatize the mixture of tertiary isononanoic acids prepared in accordance with the invention by reaction with halogenating agents such as phosphorus pentachloride, phosphorus oxychloride, sulfuryl chloride or thionyl chloride to give isononanoyl halides, from which isononanoic anhydride is obtainable by reaction with the mixture of tertiary isononanoic acids prepared in accordance with the invention, or mixed anhydrides are obtainable by reaction with other carboxylic acids. The reaction of the mixture of tertiary isononanoic acids prepared in accordance with the invention with acetic anhydride also gives, as an intermediate, the mixed anhydride, which can be converted with further addition of acid and acetic acid elimination to isononanoic anhydride or to a further mixed anhydride (Ullmanns Encyklopädie der technischen Chemie, 4th Edition, 1975, Verlag Chemie, Volume 9, pages 145-146). Proceeding from isononanoyl chloride or isononanoic anhydride, it is possible to obtain the corresponding isononanamides by reaction with ammonia, primary or secondary amines (Methoden der Organischen Chemie [Methods of Organic Chemistry], Houben-Weyl, 4th Edition, 1958, Georg Thieme Verlag, Stuttgart, Volume XI/2, pages 10-14, 16-19). Correspondingly, reaction with alcohols leads to the carboxylic esters. (Methoden der Organischen Chemie, Houben-Weyl, $4^{th}$ edition, 1952, Georg Thieme Verlag, Stuttgart, Volume VIII, pages 547-549).

Tertiary isononanoic acids are produced on an industrial scale in large amounts due to the numerous derivatization possibilities to give valuable conversion products. The process according to the invention allows access to tertiary isononanoic acids in a simple manner, proceeding from 2-ethylhexanol, which can also be operated on an industrial scale.

In the examples below, the preparation of a mixture comprising positional isomers of aliphatic tertiary isononanoic acids by reacting 2-ethylhexanol with concentrated formic acid in the presence of concentrated sulfuric acid is described.

EXAMPLES

Example 1

14.6 moles of sulfuric acid in the form of 96% sulfuric acid were initially charged in a glass flask and cooled with ice. A mixture of 4.9 moles of formic acid in the form of 96% formic acid and 1 mol of 2-ethylhexanol was then added dropwise with cooling on ice such that the temperature of the reaction mixture did not exceed 10° C. After addition was complete, the mixture was stirred for a further 4.5 h with cooling on ice and then for a further 16 hours at room temperature. The mixture was then poured onto ice. After phase separation, the organic phase was washed with water until neutral and dried over magnesium sulfate.

Example 2

The procedure was as in example 1. After complete addition of the mixture of 2-ethyl-hexanol and concentrated formic acid to the ice-cooled concentrated sulfuric acid, the mixture was allowed to stir for a further 3 hours with cooling on ice. Subsequently, the reaction mixture was allowed to stand at room temperature for 64 hours. The mixture was then poured onto ice and the organic phase was removed. The organic phase was washed with water until neutral. Subsequently, residual water was removed from the organic phase by centrifugation.

The crude products obtained according to example 1 and 2 have the following composition determined by gas chromatography (area %, according to DIN 51405).

TABLE 1

Composition by gas chromatography of the mixture of positional isomers of aliphatic tertiary isononanoic acids obtained according to example 1 and 2

| Example | 1 | 2 |
|---|---|---|
| Postreaction | 4.5 h stirring with ice cooling, 16 h stirring at room temperature | 3 h stirring with ice cooling, 64 h standing at room temperature |
| Work-up | Drying of organic phase by addition of $MgSO_4$ after washing until neutral | Removal of residual water by centrifugation after washing until neutral |

TABLE 1-continued

Composition by gas chromatography of the mixture of
positional isomers of aliphatic tertiary isononanoic acids
obtained according to example 1 and 2

| Example | 1 | 2 |
|---|---|---|
| Composition by GC (area %, according to DIN 51405) | | |
| First runnings/intermediate fraction | 0.8 | 0.3 |
| 2,2-Dimethylheptanoic acid | 26.4 | 17.4 |
| 2-Ethyl-2-methyl-hexanoic acid | 66.8 | 73.1 |
| Positional isomers of aliphatic tertiary isononanoic acids | 3.0 | 2.5 |
| Tailings | 3.0 | 6.7 |

As the results in Table 1 show, high-boiling tailings components are only formed to a small extent. The isomer distribution is also limited to few constitutional isomers. 2-Ethyl-2-methylhexanoic acid is formed as main product and 2,2-dimethylheptanoic acid is present as secondary component. Other positional isomers of aliphatic tertiary isononanoic acids are only formed to a minor degree.

The invention claimed is:

1. A process for producing a mixture comprising tertiary isononanoic acids proceeding from 2-ethylhexanol, characterized in that
   a) 2-ethylhexanol is reacted at a temperature of 0° C. to 40° C. with a mixture of concentrated formic acid and a concentrated Brønsted acid, wherein 2 to 10 mol of formic acid are used per mole of 2-ethylhexanol and the concentrated Brønsted acid is used in an amount that corresponds to 6 to 90 mol of protons per mole of 2-ethylhexanol,
   b) the reaction mixture obtained according to step a) is subsequently brought into contact with water, and
   c) the mixture comprising tertiary isononanoic acids formed according to step b) is removed.

2. The process as claimed in claim 1, characterized in that the Brønsted acid used is sulfuric acid, hydrofluoric acid, phosphoric acid, trifluoromethanesulfonic acid or fluorosulfonic acid.

3. The process as claimed in claim 1, characterized in that 3 to 6 mol of formic acid, and the Brønsted acid in an amount that corresponds to 12 to 40 mol of protons, are used per mole of 2-ethylhexanol.

4. The process as claimed in claim 1, characterized in that concentrated formic acid is used at a concentration of 95% by weight to 98% by weight.

5. The process as claimed in claim 1, characterized in that concentrated Brønsted acid is used at a concentration of 96% by weight to 98% by weight.

6. The process as claimed in claim 1, characterized in that the Brønsted acid used is concentrated sulfuric acid at a concentration of 96% by weight to 98% by weight.

7. The process as claimed in claim 1, characterized in that 3 to 6 mol of concentrated formic acid at a concentration of 95% by weight to 98% by weight and concentrated sulfuric acid at a concentration of 96% by weight to 98% by weight are used per mole of 2-ethylhexanol, wherein the sulfuric acid is used in an amount that corresponds to 12 to 40 mol of protons per mol of 2-ethylhexanol.

8. The process as claimed in claim 1, characterized in that step a) is carried out at temperatures of 5° C. to 40° C.

9. The process as claimed in claim 1, characterized in that step a) is carried out at atmospheric pressure.

10. The process as claimed in claim 1, characterized in that step a) is carried out at a positive pressure from above atmospheric pressure to 1 MPa.

11. The process as claimed in claim 2, characterized in that 3 to 6 mol of formic acid, and the Brønsted acid in an amount that corresponds to 12 to 40 mol of protons, are used per mole of 2-ethylhexanol.

12. The process as claimed in claim 2, characterized in that concentrated formic acid is used at a concentration of 95% by weight to 98% by weight.

13. The process as claimed in claim 3, characterized in that concentrated formic acid is used at a concentration of 95% by weight to 98% by weight.

14. The process as claimed in claim 2, characterized in that concentrated Brønsted acid is used at a concentration of 96% by weight to 98% by weight.

15. The process as claimed in claim 3, characterized in that concentrated Brønsted acid is used at a concentration of 96% by weight to 98% by weight.

16. The process as claimed in claim 4, characterized in that concentrated Brønsted acid is used at a concentration of 96% by weight to 98% by weight.

17. The process as claimed in claim 2, characterized in that the Brønsted acid used is concentrated sulfuric acid at a concentration of 96% by weight to 98% by weight.

18. The process as claimed in claim 3, characterized in that the Brønsted acid used is concentrated sulfuric acid at a concentration of 96% by weight to 98% by weight.

19. The process as claimed in claim 1, characterized in that step a) is carried out at temperatures of 5° C. to 20° C.

20. The process as claimed in claim 1, characterized in that step a) is carried out at a positive pressure of 0.1 to 0.5 MPa.

* * * * *